United States Patent

Bonnett et al.

Patent Number: 4,837,221
Date of Patent: Jun. 6, 1989

[54] METHODS OF TREATING TUMORS SUSCEPTIBLE TO NECROSIS

[75] Inventors: Raymond Bonnett; Morris C. Berenbaum, both of London, United Kingdom

[73] Assignee: Efamol Ltd., Surrey, England

[21] Appl. No.: 31,172

[22] Filed: Mar. 26, 1987

Related U.S. Application Data

[63] Continuation of Ser. No. 800,967, Nov. 22, 1985, abandoned.

[30] Foreign Application Priority Data

Nov. 26, 1984 [GB] United Kingdom ............... 8429845

[51] Int. Cl.$^4$ ............................................. A61K 31/40
[52] U.S. Cl. ............................................. 514/410
[58] Field of Search ................................... 514/410

[56] References Cited

U.S. PATENT DOCUMENTS 3,988,436 10/1976 Loo ....................................... 424/59
4,393,071 7/1983 Fujii et al. ........................... 514/410
4,656,186 4/1987 Bommer et al. ..................... 514/410

FOREIGN PATENT DOCUMENTS 87793 7/1982 Japan ................................... 514/410

OTHER PUBLICATIONS

Chemical Abstracts 100: 85666c (1984).
Chemical Abstracts 103: 50054m (1985).

Primary Examiner—Jerome D. Goldberg
Attorney, Agent, or Firm—Nixon & Vanderhye

[57] ABSTRACT

This invention provides for therapy of tumours susceptible to necrosis by a porphyrin when an appropriate porphyrin compound is administered to locate in the tumor followed by illumination with light of a wavelength absorbed by the compound, making use of meso-porphyrins of the formula:

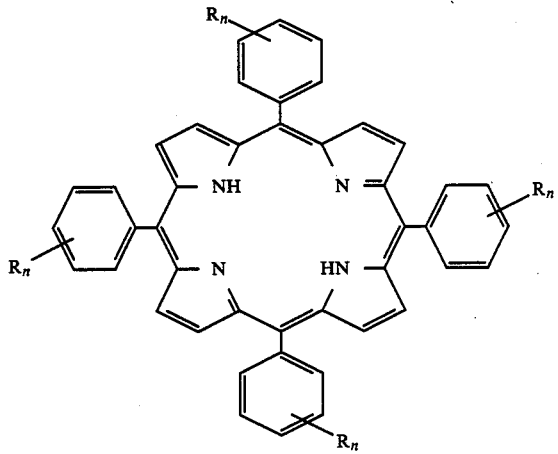

where n=1 to 3 and each substitutent R, the same or different and at the same or different position in its respective substituent phenyl ring or other aromatic group replacing that ring, is an hydroxy, amino or sulphydryl group, by association of said meso-porphyrins with a suitable pharmaceutical diluent or carrier.

2 Claims, 1 Drawing Sheet

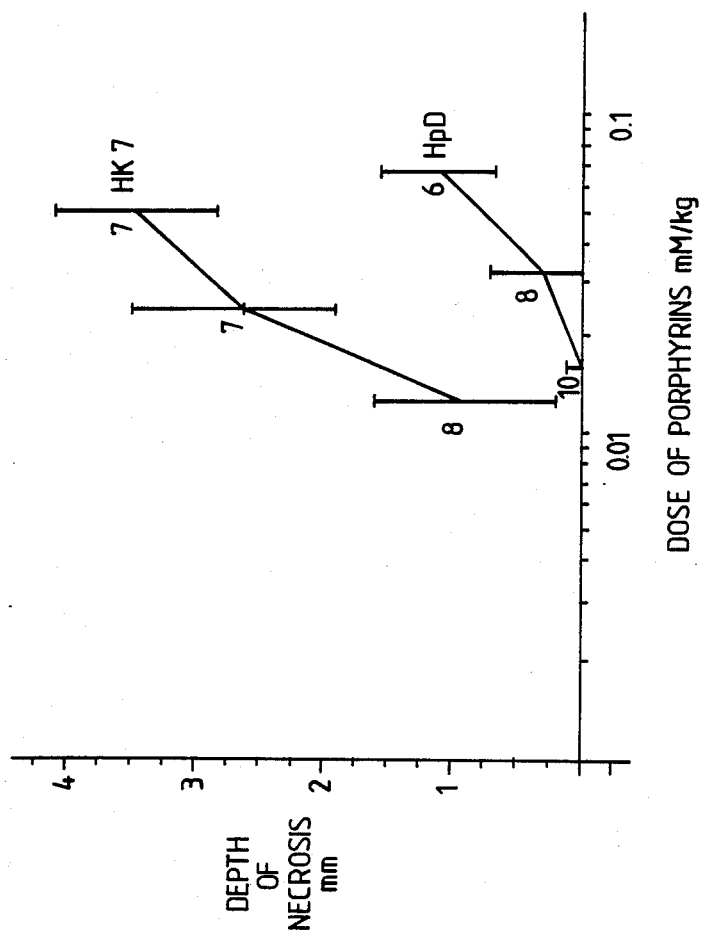

METHODS OF TREATING TUMORS SUSCEPTIBLE TO NECROSIS

This is a continuation of application Ser. No. 800,967, filed Nov. 22, 1985, now abandoned.

FIELD OF THE INVENTION

This treatment relates to certain porphyrins and their use in the treatment of tumors in man susceptible to necrosis by a porphyrin.

BACKGROUND

Haematoporphyrin derivative of uncertain specific composition (HpD) have been used in the treatment of tumors in man susceptible to necrosis by a porphyrin, having been found to locate in tumours (and other tissues) after injection into the bloodstream and to sensitise cells to light irradiation (transport in the blood is believed to be largely in association with the serum albumin). Irradiation, with a laser or other source, may be direct or indirect, for example using fibre optics. Irradiated cells (unless deeply pigmented) are rapidly killed to a depth depending on the light penetration. The mechanism of cell killing in phototherapy is believed to be largely by production of singlet oxygen. This is produced by transfer of energy from the light-excited porphyrin molecule to an oxygen molecule. Singlet oxygen is highly reactive. It is believed to oxidise cell membranes so that they are damaged and become incapable of exerting their function of controlling the cell's internal environment. This rapidly leads to cell death.

In addition to the use of HpD there is prior art in the literature of tumour-locating tetraphenyl porphyrins in Chemical Abstracts 90 12 (1979) 132517s where carboxyl and sulphonate (hydroxysulphonyl) substitutents are shown in phenyl rings, and in Chemical Abstracts 97 795 (1982) 182083n where unsymmetrical functionalised derivatives of tetraphenyl porphine are shown, which the "Health Sciences, Dentistry" article itself shows to be 5-hydroxyphenyl-10,15,20-tricarboxy phenyl porphyrins in the form of derivatives of N,N-bis(2-chloroethyl) phosphorodiamidic acid. More peripheral publications are U.S. Pat. No. 4,386,087, disclosing leukaemia treatment with sulphonated tetraphenyl porphyrins, and EP A-0 066 884, disclosing iron complexes of substituted tetra-amino porphyrins for use as oxygen absorbing and desorbing agents. Chemical Abstracts 100 358 (1984) 109155p shows similar oxygen carrying systems and U.S. Pat. No. 4,307,084 related ones using carboxyl substituted compounds.

THE INVENTION

We have sought to improve on the prior art, and in particular to improve on HpD by finding well characterised and thus more exactly controllable compounds. Other aims have been finding compounds activated by light at wavelengths longer than those used to activate HpD so as to exploit deeper penetration of longer wavelength radiation, and to increase effectiveness generally, as in many anatomical sites, such as the brain, HpD has been found to sensitise normal cells unduly as well as cancerous cells. The wavelength at which a photosensitising compound is activated is one factor in its in vivo efectiveness. Other things being equal, the longer the activating wavelength within the visible range, the greater the tissue penetration of light and therefore the greater the depth of damage. Thus, compounds activated at 650-660nm might be expected to produce greater depths of damage than HpD, which is activated at 625-630nm. Successful phototherapy depends on the ability to produce severe tumour damage without unacceptable damage to contiguous normal tissues.

Selectivity of damage for various tissues, including tumours, is governed by a variety of factors, including selective uptake, selective vulnerability and selective ability to repair damage (cf. Albert A.A. *Selective Toxicity*, fifth edition, Chapman & Hall, London 1973). In tumours an additional factor is the precarious nature of tumour blood supply and its particular vulnerability to photodynamic damage as compared with the robust and well-established blood supply of normal tissues. All the above factors vary from one tissue to another and from one compound to another, so that the pattern of tumour and normal tissue damage may be expected to vary between different photosensitising drugs.

The invention provides a method of therapy of tumours susceptible to necrosis by a porphyrin when an appropriate porphyrin compound is administered to locate in the tumour followed by illumination of the tumour with light of a wavelength absorbed by the compound, said method making use of meso-porphyrins of the formula:

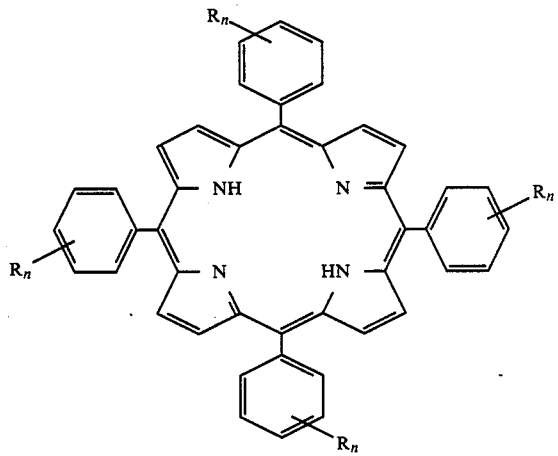

wherein each R (one or more in each ring n=1 to 3) is an ortho, meta or para positioned hydroxy (—OH), amino (—NH$_2$) or sulphydryl (—SH) substituent group, particularly to give polyhydroxy phenyl compounds. Said group may optionally itself be substituted for example by alkyl or acyl groups preferably C$_1$ to C$_4$ and the compounds when in such substituted form at one or more groups R are within the main claim herein. The R groups and any substituents thereof may be the same or different and in the same or different positions on their respective substituent rings, which may themselves be replaced by other aromatic ring systems. The nucleus or the substituent rings may be substituted further, provided pharmacological tolerability, appreciable solubility in water (required so that the drug may be administered intravenously to ensure rapid distribution to the tumour), absorption of light at the red end spectrum, and take up in cancerous tissue are retained, and the compounds when in such form are to be understood as within the claims herein. Any of the compounds further may be in the form of derivatives such as addition salts at acidic or basic centres, metal complexes (e.g. Zn, Ga), or hydrates or other solvates particularly with lower, e.g. $C_1$–$C_4$ aliphatic alcohols and again such derivatives are within the claims.

It is preferred that one or more of the substituents R should be of a kind and in a form able to ionise at physiological pH, to increase the absorption in the red part of the spectrum, that is in the portion that most effectively penetrates tissue. Compounds not very soluble in themselves may be solubilised by the presence of suitable groups such as sulphonate groups.

The invention further extends to the compounds per se when novel.

PREPARATION OF COMPOUNDS

Methods of preparation of porphyrin compounds are known in the art and may be used for example to make a preferred compound, itself known, namely 5,10,15,20-tetra (4-hydroxyphenyl) porphyrin (HK7). Similar methods may be applied to make the other compounds and examples are given below.

The ethanol tetra solvate of HK7, a new compound, may be made as follows: 5,10,15,20-tetra(4-acetoxyphenyl) porphyrin (0.5g) is refluxed for five-and-a-half hours in methylated spirits (250ml) containing potassium hydroxide (0.36g). The dark green solution is filtered, acidified with acetic acid, and taken to dryness. The residue is washed with water and crystallised from ethanol-chloroform to give purple crystals (250mg, 50%) of HK7.4EtOH.

Various specific compounds within the claims are made as follows, being first listed under the structure:

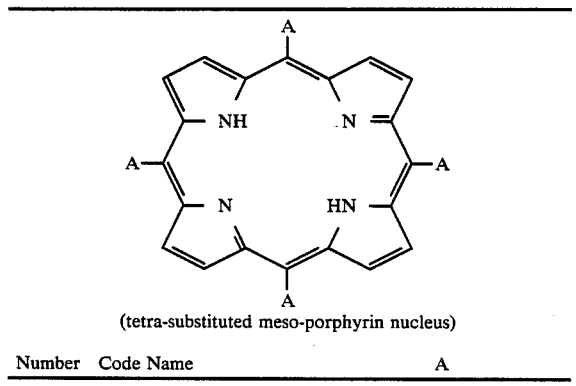

(tetra-substituted meso-porphyrin nucleus)

| Number | Code Name | A |
|---|---|---|
| 1 | HK7 | —C₆H₄—OH (para) |
| 2 | acetyl derivative of HK7 | —C₆H₄—OC(O)CH₃ (para) |
| 3 | ortho-HK7 | —C₆H₄—OH (ortho) |
| 4 | methyl derivative of ortho-HK7 | —C₆H₄—OCH₃ (ortho) |

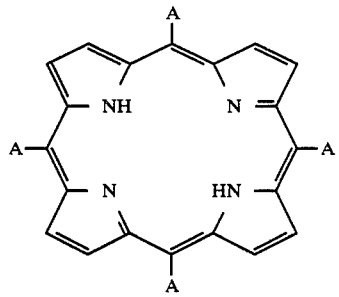

(tetra-substituted meso-porphyrin nucleus)

| Number | Code Name | A |
|---|---|---|
| 5 | meta-HK7 | —C₆H₄—OH (meta) |
| 6 | acetyl derivative of meta-HK7 | —C₆H₄—OC(O)CH₃ (meta) |
| 7 | HK8 (amino analogue of ortho-HK7) | —C₆H₄—NH₂ (ortho) |
| 8 | HK9 (acetyl amino analogue of HK7) | —C₆H₄—NHC(O)CH₃ (para) |
| 9 | HK10 (sulphydryl analogue of HK7) | —C₆H₄—SH (para) |
| 10 | HK11 (sulphydryl analogue of ortho HK7) | —C₆H₄—SH (ortho) |

PREPARATION OF 5,10,15,20-TETRA(p-ACETOXYPHENYL) PORPHYRIN (ACETYL DERIVATIVE OF HK7)

para-Acetoxybenzaldehyde (9.0g) and freshly distilled pyrrole (3.69g) are added to refluxing propionic acid (90ml). The reaction mixture is boiled under reflux for one hour and cooled overnight at 0° C. The crude porphyrin is filtered off and recrystallised from chloroform/petroleum ether (bp 30°–40° C.) to give the acetyl derivative of HK7 as purple crystals (1.62g). NMR: ($CDCl_3$) δ 8.90 (s, 8H, β pyrrole H); 8.21 (d, 8H, benzenoid H); 7.49 (d, 8H, benzenoid H); 2.5 (s, 12H, $CH_3$); −2.77 (s, 2H, NH).

PREPARATION OF 5,10,15,20-TETRA(p-HYDROXYPHENYL) PORPHYRIN (HK7)

The foregoing tetracetate (0.65g) is dissolved in a solution of sodium hydroxide (0.57g) in ethanol (300ml) and refluxed for 3.5 hours. The solution is filtered when cold, acidified with glacial acetic acid (to pH 6–7) and evaporated to dryness. The solid is washed with cold water to remove sodium acetate, and the residue is recrystallised from tetrahydrofuran/chloroform to give purple crystals (0.47g) of HK7.

NMR: ($CDCl_3$:$d_6$—DMSO=3:1) 9.18 (bs, 4H, OH); 8.92 (s, 8H, $\beta$-pyrrole H); 8.03 (d, 8H, benzenoid H); 7.25 (d, 8H, benzenoid H); −2.78 (bs, 2H, NH).

s =singlet; d=doublet; b=broad

Potassium, lithium and sodium salts of HK7 are made by dissolving HK7 in tetrahydrofluran to give a concentrated solution, and adding a slight excess of the required metal alkoxide in methanol. The precipitated salt is removed by filtration or centrifugation, washed with tetrahydrofuran, and dried (80° C., in vacuo).

The zinc complex of HK7 is made by treating HK7 with zinc acetate in methanol-acetic acid. The metallation is monitored by analytical thin layer chromatography and is generally complete within 10 minutes. The zinc complex of HK7 is recrystallised from tetrahydrofuran-chloroform to give purple crystals. NMR ($CDCl_3$:$d_6$—DMSO=3:1) 9.07 (s, 4H, OH); 8.92 (s, 8H, $\beta$-pyrrole H); 8.02 (d, 8H, benzenoid H); 7.21 (d, 8H, benzenoid H). NH signals absent as expected.

PREPARATION OF m-HYDROXYPHENYL COMPOUNDS CORRESPONDING TO THE ABOVE

The acetyl derivative of meta-HK7 and meta-HK7 itself are prepared in the analogous way to the foregoing starting from meta-acetoxybenzaldehyde.

PREPARATION OF 5,10,15,20-TETRA(o-METHOXYPHENYL) PORPHYRIN (METHYL DERIVATIVE OF ORTHO HK7)

ortho-Methoxybenzaldehyde (1.03g) is refluxed in propionic acid (30ml) and pyrrole (0.44g) is added. The mixture is refluxed for 1 hour, and kept at room temperature overnight. The black precipitate is removed by filtration, and the filtrate is taken to dryness under reduced pressure, and chromatographed on a column of silica gel G. Elution with diethyl ether brings off a purple band, which is re-chromatographed and crystallised from methanolchloroform to give the methyl derivative of ortho HK7 as dark purple crystals (0.036g). NMR($CDCl_3$) $\delta$ 8.71 (s, 8H, $\beta$ pyrrole H); 7.2-8.13 (m, 16H, benzenoid H); 3.58 (three signals 12H, $OCH_3$-astropisomers).

PREPARATION OF 5,10,15,20-TETRA(o-HYDROXYPHENYL) PORPHYRIN (ORTHO-HK7)

Boron tribromide (0.7ml) is added to dry dichloromethane, and the mixture is cooled to ca −80° C. The methyl derivative of orthos HK7 (0.209g) is dissolved in the minimum volume of dry dichloromethane and added slowly to the $BBr_3$ solution over 45 minutes. The green solution is stirred at −80° C. for 1 hour, and then allowed to come to room temperature with stirring over 24 hours. The mixture is treated at ca 0° C. with excess methanol (to destroy excess $BBr_3$). The mixture is neutralised with triethylamine, and evaporated to dryness and recrystallised from methanol-water to give purple crystals (0.036g).

NMR: ($CDCl_3$:$d_6$—DMSO=3:1) 8.84 (s, $\beta$-pyrrole H); 7–8 (m, benzenoid protons); 2.77 (bs, OH).

PREPARATION OF 5,10,15-20-TETRA(o-AMINOPHENYL) PORPHYRIN (COMPOUND HK8)

5,10,15,20-Tetra (o-nitrophenyl) porphyrin (0.92g) is heated at 65° for 25 minutes with tin (II) chloride dihydrate (4.25g) in concentrated hydrochloric acid (50ml). The cooled mixture is treated with excess aqueous ammonia and repeatedly extracted with chloroform. The chloroform solution is washed with aqueous ammonia and with water, taken to dryness and recrystallised from methanol-chloroform to give purple crystals (0.32g).

NMR: ($CDCl_3$) $\delta$ 8.90 (s, 8H, $\beta$-pyrrole H); 7–8 (m, 16H, benzenoid H); 2–4 (bs $NH_2$ groups in benzenoid rings); −2.6 (bs, porphyrin NH).

PREPARATION OF 5,10,15,20-Tetra(p-ACETAMIDOPHENYL) PORPHYRIN (HK9)

para-Acetamidobenzaldehyde (10.0g) is added to refluxing propionic acid (100ml): an orange solution gradually forms. Pyrrole (4.1g) is added continuously, and the dark solution is refluxed for 1 hour, and kept at 0° C. overnight. A dark tarry material is removed by filtration and the filtrate is evaporated to dryness. The residue is dissolved in chloroform and chromatographed on silica gel G eluted with 10% methanol in chloroform. The red fluorescing fractions are combined and the porphyrin HK9 is obtained as a purple solid (0.021g) on evaporation.

NMR: ($d_6$—DMSO) $\delta$ 10.36 (s, 4H, NH of $NHCOCH_3$); 8.88 (s, 8H, $\beta$-pyrrole H); 7.9–8.3 (m, 16H, benzenoid H), 2.23 (s, 12H, $CH_3$ of $NHCOCH_3$).

PREPARATION OF THIO AND METHYLTHIO ANALOGUES OF ORTHO HK7 AND PARA HK7

The thio (sulphydryl) and methylthio analogues of ortho HK7 and para HK7 are made analogously to the ortho methoxyphenyl and hydroxyphenyl compounds above, using methylthio ethers of benzaldehyde as starting materials and cleaving off the methyl groups as required. The thioethers are prepared according to R.C. Crawford and C. Woo, Can. J. Chem. 1965, Vol. 43, p3178 for the ortho compound and W.P. Buu-Hoi, N.D. Xuong, N.B. Tien, Michel Sy and Guy Lejeune, Bull. Soc. Chim. France, 1955, p1594 for the para compound.

USE IN THERAPY

In human therapy HpD has been used to treat some 2–3000 patients world-wide. Some recent results are given in Doiron D.R. and Gomer C.J. (eds) *Porphyrin Localization and Treatment of Tumours.* Alan R. Liss, Inc., New York, 1984. The compounds used according to the invention are employed in a similar way, and tests as below in mice have shown their efficacy. These tests give a fair indication of expected value in human therapy for which dosages are given later herein.

EVIDENCE ON TETRA-(p-HYDROXY PHENYL) DERIVATIVE

The evidence is (i) that HK7 is a more effective photosensitiser for tumour tissue in animal assay than is HpD; (ii) that unlike HpD, HK7 does not cause detectable cerebral photosensitivity in animals in dose regimes that effectively sensitise tumours and that it therefore has promise in the treatment of brain tumours; and (iii) that the skin photosensitisation produced by HK7 is less persistant than that caused by HpD.

However, HK7 is relatively insoluble in neutral aqueous media and, in the present experiments, it was given either in 0.0125–0.05 M.NaOH or in physiological saline intravenously, or in DMSO intraperitoneally.

(a) Tumour necrosis

The method was as described in Berenbaum, Bonnett and Scourides (Br. J. Cancer, 1982, 45, 571) using a transplantable mouse tumour originating in plasma cells. The photosensitising drug is given intravenously in aqueous medium or intraperitoneally in DMSO, the tumour exposed to light at the appropriate wavelength and the depth of tumour necrosis measured. The light dose is $10J/cm^2$, at 630nm for HpD (assumed M.W.600) and at 658nm for HK7 (M.W.679). Results are shown in graph. The relative potency is determined by comparing amounts of drugs required to produce equal effects. Thus, 0.0125 $\mu$M/kg HK7 i.v. (i.v. =intravenous, i.p. =intraperitoneal, for DMSO preparations) had about the same effect as 0.067 $\mu$M/kg HpD, so HK7 was about 5 times as effective as HpD in this experiment.

As shown by van Gemert, Berenbaum & Gijsbers (Br.J. Cancer 1985, 52, 43) quantitative results obtained in this test may be extrapolated to man with a reasonable confidence.

(b) Cerebral photosensitisation (i) Mice were given 0.033 $\mu$M/kg i.v. of HpD or HK7 and 24 hours later the cranium exposed to $20J/cm^2$ of white light. Deaths within 48 hours (due to acute cerebral oedema) were:

| HK7 | HpD |
|-----|-----|
| 0/5 | 4/5 |

(ii) Mice treated with HK7 or HpD as above (or with saline i.v.) were given Evans blue complexed to bovine serum albumin i.v. 4 hours after exposure of the cranium to $20J/cm^2$ white light, and the amount of Evans blue in the brain measured 1 hour later. Normally, very little is found, and this is largely dye still circulating in the blood 1 hour after injection, and not in the brain substance itself. An increase is produced by agents that damage the brain vascular lining, allowing dye to enter the brain substance.

Results ($\mu$g dye/brain) in groups of 5 mice were:

| Saline | HK7 | HpD |
|--------|-----|-----|
| 25.2 ± 3.42 | 23.6 ± 3.65 | 69.8 ± 24.24 |

Thus, 24 hours after a dose of HpD that normally produces relatively little tumour sensitisation (see graph), there is a lethal cerebral photosensitivity and damage to brain blood vessels. In contrast, 24 hours after a dose of HK7 that produces substantial tumour sensitisation, there is no cerebral photosensitivity detectable by these methods.

(c) Skin photosensitisation

An unexpected benefit over HpD has been found from the results of a comparison of skin photosensitisation induced by HpD and HK7 in equimolar doses. Mice were given doses of porphyrin and depilated skin exposed to $10J/cm^2$ of light at the appropriate wavelength (625nm for HpD, 656nm for HK7) at various times after the injection. The increase in skin thickness was measured 4 hours after illumination.

It was shown that, 1 day after porphyrin injection, HK7 is a more potent skin sensitiser than HpD. By 1 week, there is little difference. By 2 weeks, the maximum dose of HK7 no longer sensitises to this dose of light. However, HpD still produces significant sensitisation at 2 and 3 weeks.

The conclusion is that HK7 is a more potent skin photosensitiser than HpD, but that the effect is more transient, a desirable feature.

(d) Comparison of HK7 and HK7.4EtOH

A preliminary comparison was made. Both materials dissolved easily in DMSO, and dilution in 0.05M.NaOH gave dark green solutions. The light dose was $10J/cm^2$ at 660nm. Depths of tumour necrosis (in mm) were:

| Dose ($\mu$M/kg) | Solvent | HK7 | HK7.4EtOH |
|---|---|---|---|
| 67 | DMSO | 4, 5, 6 | 3.75, 4, 4, 5 |
| 33 | NaOH-DMSO | 0.5, 0.5, 1.5, 4.5 | 0.25, 0.5, 0.75, 2, 2, 2 |

Thus, no significant difference was found between the two substances in this system.

EVIDENCE GENERALLY

The compounds prepared above have been tested in a fuller series of trails as follows:

RESULTS OF INDIVIDUAL TESTS
(Numbers of animals in brackets)

| Material | Dose ($\mu$M/kg) | Solvent | Wavelength of light (nm) | Necrosis (after $10J/cm^2$ (mm ± S.E.M. (n)) |
|---|---|---|---|---|
| HK7 | 50 | DMSO | 656 | 5.06 ± 0.48 (4), 4.33 ± 0.17 (6) |
| | 25 | DMSO | 656 | 3.54 ± 0.48 (6), 2.63 ± 0.56 (8) 4.38 ± 0.24 (6) |
| | 12.5 | DMSO | 656 | 2.86 ± 0.26 (7), 2.50 ± 0.52 (5) 4.13 ± 0.59 (4) |
| | 6.25 | DMSO | 656 | 1.17 ± 0.31 (6), 0.85 ± 0.38 (5) |
| | 50 | NaOH | 669 | 4.43 ± 0.45 (7), 3.32 ± 0.63 (7) 3.25 ± 0.37 (8) |
| | 25 | NaOH | 669 | 2.75 ± 0.25 (5), 2.38 ± 0.24 (4) |
| | 25 | NaOH | 654 | 3.64 ± 0.39 (7) |
| | 12.5 | NaOH | 654 | 2.40 ± 0.10 (5) |
| Li-HK7 | 50 | DMSO | 656 | 2.46 ± 0.38 (6), 3.50 ± 0.41 (6) |
| | 25 | DMSO | 656 | 3.31 ± 0.40 (4), 3.00 ± 0.72 (6) 3.00 ± 0.51 (8) |
| Na-HK7 | 50 | NaOH | 664 | 3.15 ± 0.83 (5) |
| | 50 | DMSO | 656 | 2.80 ± 0.12 (5), 3.79 ± 0.29 (7) |

-continued

RESULTS OF INDIVIDUAL TESTS
(Numbers of animals in brackets)

| Material | Dose (μM/kg) | Solvent | Wavelength of light (nm) | Necrosis (after 10J/cm² (mm ± S.E.M. (n)) |
|---|---|---|---|---|
| | 25 | DMSO | 656 | 2.28 ± 0.47 (8) |
| K-HK7 | 50 | NaOH | 654 | 5.06 ± 0.12 (8) |
| | 50 | DMSO | 656 | 4.38 ± 0.37 (2) |
| | 25 | DMSO | 656 | 3.32 ± 0.59 (7) |
| | 12.5 | DMSO | 656 | 2.50 ± 0.44 (8) |
| HK7 | 50 | NaOH | 620 | 4.40 ± 0.42 (5) |
| zinc complex | 25 | DMSO | 607 | 2.67 ± 0.28 (6) |
| meta-HK7 | 50.0 | DMSO | 648 | 4.63 ± 0.64 (6) |
| | 25.0 | DMSO | 648 | 5.37 ± 0.55 (4) |
| | 12.5 | DMSO | 648 | 4.44 ± 0.35 (8) |
| | | | | 4.5 ± 0.5 (5) |
| | 6.25 | DMSO | 648 | 3.53 ± 0.49 (10) |
| | | | | 2.88 ± 0.9 (6) |
| | | | | 3.86 ± 0.18 (7) |
| | 3.12 | DMSO | 648 | 2.46 ± 1.55 (13) |
| | | | | 1.08 ± 0.51 (6) |
| | | | | 1.69 ± 0.47 (8) |
| | 1.56 | DMSO | 648 | 0.65 ± 0.22 (15) |
| meta-HK7 | 12.5 | NaOH | 648 | 3.25 ± 0.33 (8) |
| | 6.25 | NaOH | 648 | 3.78 ± 0.36 (8), |
| | | | | 3.64 ± 0.34 (7) |
| | 3.25 | NaOH | 648 | 2.61 ± 0.54 (8), |
| | | | | 0.69 ± 0.35 (8) |
| ortho-HK7 | 50.0 | DMSO | 648 | 4.25 ± 0.50 (7) |
| | 25.0 | DMSO | 648 | 4.21 ± 0.32 (6) |
| | 25.0 | DMSO | 648 | 3.21 ± 0.56 |
| | 12.5 | DMSO | 648 | 3.03 ± 0.29 (15) |
| | 6.25 | DMSO | 648 | 2.45 ± 0.28 (14) |
| Sodium salt of HK7 zinc complex | 50.0 | DMSO | 608 | 0.69 ± 0.31 (5) |
| | 50.0 | 0.05M NaOH | 608 | 1.0 ± 0.34 (5) |

It should be noted that the experimental tumours averaged 5mm in depth and, in the higher dose-ranges, many showed full-depth necrosis. Therefore, in these dose-ranges, the values for depth of tumour necrosis given in the table are probably underestimates.

It may be seen that HK7 is rather more effective administered in DMSO than in alkali but that m-HK7 is equally effective in both. The depth of necrosis is dose-related, and in general a balance must be struck between doses being high enough to show userful necrosis and not so high as to be prohibitively toxic. For example, the lithium, sodium and zinc salts of HK7 show necrosis depth below 1.0 mm at 12.5 μm/kg while HK7 itself is reasonably effective at 6.25 μm/kg and meta-HK7 is effective at 3.12 μm/kg and with some effect even at 1.56 μm/kg. It is the most active compound found. Assuming that the potency ratios between these compounds and HpD found in mice hold approximately for man also, we would expect the most effective doses in man to lie in the range 0.25–1.0mg/kg, subject to the fact that the safe and effective range for a given compound must be found by trial. At its widest, subject always to that proviso, the range will not be outside 0.01 to 10.0 (or possibly up to 100) mg/kg. Ranges for the dose of illumination are, for example, 2.5 to 500 J/cm² conveniently 5 to 250 J/cm² depending primarily on tumour thickness. In some instances more than one such dose of light may be desirable following a single, or possibly, more than one such administration of the porphyrin.

For comparison HpD given in 0.5% NaHCO₃ at 67 μm/kg and illuminated at 630 nm gave a tumour necrosis depth of 2.79 ±1.36 mm (7) (molecular weight of HpD assumed 600), while the sodium salt of tetra-(p-hydroxysulphonyl phenyl) porphyrin in saline at molar equivalent dose and illuminated at 550 nm gave a necrosis depth of only 0.30±0.11 mm. (See FIG. 1)

We claim:

1. A method of treating tumors in man susceptible to necrosis by a porphyrin comprising:
   (a) administering to a person suffering from said tumor a pharmacologically acceptable and effective amount, within the range of 0.01 to 100 mg/kg body weight, of said porphyrin of the formula:

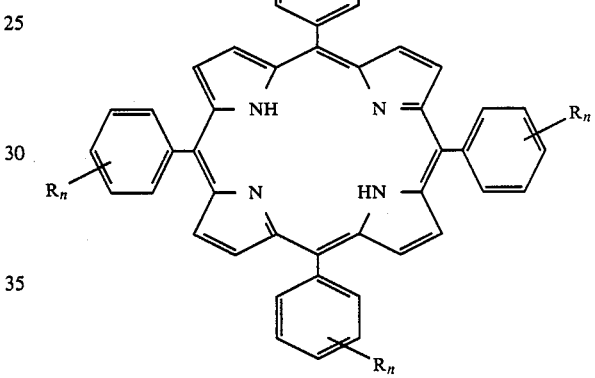

where n=1 to 3 and each substituent R, which may be the same or different and at the same or different position in its respective substituent phenyl ring, is hydroxy, amino or sulphydryl, in a suitable pharmaceutical diluent or carrier, to locate in the tumor, followed by
   (b) illuminating the tumor with light of a wavelength in the range of 600–700 nm which is absorbed by the porphyrin.

2. The method according to claim 1, where each substituent

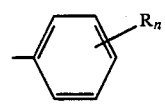

is o-hydroxyphenyl, m-hydroxyphenyl or p-hydroxyphenyl.

* * * * *